US012597240B2

(12) United States Patent
Huelnhagen et al.

(10) Patent No.: US 12,597,240 B2
(45) Date of Patent: Apr. 7, 2026

(54) METHOD AND SYSTEM FOR AUTOMATED CENTRAL VEIN SIGN ASSESSMENT

(71) Applicants: Siermens Healthineers AG, Erlangen (DE); Centre Hospitalier Universitaire Vaudois, Lausanne (CH)

(72) Inventors: Till Huelnhagen, Erlangen (DE); Jonas Richiardi, Geneva (CH)

(73) Assignees: Siermens Healthineers AG, Erlangen (DE); Centre Hopitalier Universitaire Vaudois, Lausanne (CH)

( * ) Notice: Subject to any disclaimer, the term of this patent is extended or adjusted under 35 U.S.C. 154(b) by 371 days.

(21) Appl. No.: 18/303,724

(22) Filed: Apr. 20, 2023

(65) Prior Publication Data

US 2023/0343077 A1 Oct. 26, 2023

(30) Foreign Application Priority Data

Apr. 20, 2022 (EP) ..................................... 22168961

(51) Int. Cl.
$\quad$ G06V 10/776 (2022.01)
$\quad$ G06T 7/00 (2017.01)
$\quad\quad$ (Continued)

(52) U.S. Cl.
$\quad$ CPC .......... G06V 10/776 (2022.01); G06T 7/0012 (2013.01); G06V 10/267 (2022.01); G06V 10/764 (2022.01); G06V 10/82 (2022.01); G06V 10/87 (2022.01); G16H 50/70 (2018.01); G06T 2207/10088 (2013.01); G06T

2207/20081 (2013.01); *G06T 2207/30016* (2013.01); *G06T 2207/30096* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 10,761,171 B2 * | 9/2020 | Gulani | ............... G01R 33/5676 |
| 2022/0270254 A1 * | 8/2022 | Palma | .................... G06T 7/174 |

OTHER PUBLICATIONS

Solomon AJ, Bourdette DN, et al. The contemporary spectrum of multiple sclerosis misdiagnosis. Neurology 2016 (87): 1393-1399.

(Continued)

*Primary Examiner* — Nancy Bitar
(74) *Attorney, Agent, or Firm* — Laurence A. Greenberg; Werner H. Stemer; Ralph E. Locher

(57) ABSTRACT

A system and method automatically detect, in MR images, WM lesions exhibiting a central vein sign. A set of MR images of a brain lesion is acquired, using images of the set as input to different ML algorithms. A first ML algorithm classifies inputted image(s) into first or second classes. The first class includes CVS+/- and the second class CVSe lesions. A second ML algorithm classifies inputted image(s) into third or fourth classes. The third class includes CVS+ lesions and the fourth central vein sign- lesions. For each set, probability values are used that the set belongs to classes as inputs to a final classifier performing a final classification of the set into second, third, or fourth classes. For each class, the final classifier outputs final probability that the set belongs to the class. The second, third or fourth class with highest probability value is provided through an interface.

9 Claims, 2 Drawing Sheets

(51) Int. Cl.

| | |
|---|---|
| *G06V 10/26* | (2022.01) |
| *G06V 10/70* | (2022.01) |
| *G06V 10/764* | (2022.01) |
| *G06V 10/82* | (2022.01) |
| *G16H 50/70* | (2018.01) |

(56) References Cited

OTHER PUBLICATIONS

Maayan Frid-Adar et al: "Modeling the Intra-class Variability for Liver Lesion Detection using a Multi-class Patch-based CNN", arxiv.org, Cornell University Library, 201 Olin Library Cornell University Ithaca, NY 14853, Jul. 19, 2017 (Jul. 19, 2017), XP080777941, DOI: 10.1007/978-3-319-67434-6_15.

Dworkin JD, Sati P, Solomon A, et al., Automated integration of multimodal MRI for the probabilistic detection of the central vein sign in white matter lesions, Am. J. Neuroradiol. 2018.

Sati P, George IC, Shea CD, Gaitan ML, Reich DS. Flair*: A combined MR contrast technique for visualizing white matter lesions and parenchymal veins. Radiology 2012, doi: 10.1148/radiol. 12120208.

Sati, Dr. Pascal et al., Detection of Central Vein sign: Specificity and Sensitivity, NAIMS symposium, NIH, NINDS, Bethesda, MD, University of Vermont, Burlington VT, Multiple Sclerosis Journal 2015; 25:(SI) 3-19.

Roche A, Forbes F. Partial Volume Estimation in Brain MRI Revisited BT—Medical Image Computing and Computer-Assisted Intervention—MICCAI 2014: 17th International Conference, Boston, MA, USA, Sep. 14-18, 2014, Proceedings, Part I. In: Golland P, Hata N, Barillot C, Hornegger J, Howe R, editors. Cham: Springer International Publishing; 2014. pp. 771-778.

Huelnhagen et al., Toward Fully Automated Assessment of the Central Vein Sign Using Deep Learning, Proc. Intl. Soc. Mag. Reson. Med. 29 (2021), 0488.

Snehashis et al . . . Multiple sclerosis lesion segmentation from brain MRI via fully convolutional neural networks. arXiv: 1803.09172 2018.

Maggi Pietro et al. CVSnet: A machine learning approach for automated central vein sign assessment in multiple sclerosis, NMR Biomed. 2020.

Sati P. Oh J, Todd Constable R, et al. The central vein sign and its clinical evaluation for the diagnosis of multiple sclerosis: A consensus statement from the North American Imaging in Multiple Sclerosis Cooperative. Nat. Rev. Neurol. 2016.

* cited by examiner

201

<u>200</u>

206

METHOD AND SYSTEM FOR AUTOMATED CENTRAL VEIN SIGN ASSESSMENT

CROSS-REFERENCE TO RELATED APPLICATION

This application claims the priority, under 35 U.S.C. § 119, of European Patent Application EP 22 168 961.5, filed Apr. 20, 2022; the prior application is herewith incorporated by reference in its entirety.

FIELD AND BACKGROUND OF THE INVENTION

The present invention falls within the field of medical imaging systems and methods, notably magnetic resonance imaging (MRI) systems and methods. In particular, the present invention relates to a method for automated central vein sign assessment, and to a device for carrying out the method.

Misdiagnosis with potentially harmful consequences for patients is a common problem in multiple sclerosis (MS) and was estimated to affect up to 20% of patients [1]. Assessment of the fraction of white matter (WM) lesions exhibiting a central vein, referred to as the central vein sign (CVS)—i.e. a small vein located at the center of the WM lesion —, has shown the potential to distinguish MS from other mimicking diseases and thereby potentially reduce misdiagnoses. Manual CVS assessment can, however, be tedious and very time-consuming, rendering it unfeasible in clinical routine. In order to address this problem, automated approaches have been proposed [2,3], but the task remains non-trivial. In particular, the selection of lesions that should be excluded from the assessment per the NAIMS criteria [4]—the lesions being called hereafter CVS excluded (CVSe) lesions—has proven to be challenging, resulting in limited classification accuracy of automated approaches. The selection of lesions to include or exclude is an important requirement to determine the fraction of CVS positive lesions, which is then used as a metric for differential diagnosis.

Those limitations have so far hindered broader clinical assessment and evaluation of the CVS as an imaging biomarker for differential diagnosis.

Automated CVS assessment using probabilistic or deep learning-based approaches are known in the art. For instance, Dworkin, et al. [5] uses a Frangi vesselness filter to detect veins combined with a textural analysis to identify lesion centers. In that approach all periventricular lesions are excluded as they are considered to be confluent or contain multiple veins. The CVS+ probabilities (i.e. the probabilities of having a lesion including one and only one vein that is centrally located within the lesion) are then weighted by image noise to account for artifacts. Another technique proposes to use ensembles of convolutional neural networks for CVS assessment (CVSNet, CVSNet2, see ref. [3] and [6]), but either requires a manual lesion exclusion step or classifies all three CVS lesion types (CVS+, CVS– and CVSe) at the same time.

While overall the classification performance of those methods is considered good, it is still not sufficient to allow confidently applying them for fully automated CVS assessment in an unsupervised setting, which hinders broader clinical application.

SUMMARY OF THE INVENTION

It is accordingly an object of the invention to provide a method and a system for automated central vein sign assessment, which overcome the hereinafore-mentioned disadvantages of the heretofore-known methods and systems of this general type and which are capable of automated CVS assessment that are suitable for clinical applications.

This object is achieved according to the present invention by a system and a method for automatically detecting in a MR image a WM lesion exhibiting a CVS according to the object of the independent claims. Dependent claims present further advantages of the invention.

With the foregoing and other objects in view there is provided, in accordance with the invention, a method comprising the following steps:

receiving or acquiring one or several 3D MR images of a brain lesion, i.e. a set of 3D MR images of a brain lesion, wherein each 3D MR image represents preferentially a different MR image contrast of the brain lesion. Each of the 3D MR images might be an image of a single brain lesion, or might be an image of multiple brain lesions. Preferentially, for each brain lesion, the set includes at least a first image acquired using a T2*-based contrast imaging technique, or, more generally speaking, using an MRI method capable of imaging the magnetic properties of blood, and optionally a second image acquired using an MRI method configured for enabling an identification of WM lesions. Preferentially, instead of the first image and the optional second image, or in addition to the first and optional second image, at least one of the 3D MR brain lesion images of the set is obtained by combining the first image and the second image. In other words and preferentially, for each brain lesion, at least a 3D image combining an MR contrast configured for imaging or detecting veins and a MR contrast configured for imaging or identifying WM lesions might be acquired. Preferentially, the set of 3D MR images of a brain lesion are image patches, i.e. 3D images including a selected set of voxels representing only the concerned brain lesion plus a predefined margin surrounding the latter, e.g. centered on the brain lesion (in other words, they represent different contrasts of a same (selected) set of voxels representing the brain lesion). Alternatively, the set of 3D MR images might be whole brain images. For instance, the first and second images typically represent brain slices, e.g. axial slices, of a brain of a patient. Preferentially, the 3D MR brain lesion images are spatially registered onto a common space. In particular, the second image is, or is based on, a fluid-attenuated inversion recovery (FLAIR) image of the brain. Preferentially, the MR images of a brain lesion include a FLAIR*image of the lesion. Preferentially, a 3D T1-weighted magnetization-prepared rapid gradient echo (MPRAGE) image, a 3D T2-weighted FLAIR image, and a 3D T2*-weighted segmented echo-planar image (EPI) of a same part of the brain, e.g. representing the same slice or volume of the brain, can be acquired by an MRI system and then registered to a common space, e.g. the FLAIR space, and combined in order to generate the FLAIR*image. Optionally, each 3D MR brain lesion image is obtained after performing, or results from, an automatic segmentation of an MRI brain image, wherein the MRI brain image is for instance the first image, or the second image, or the result of the combination of the first and second image (e.g. the MRI brain image is the FLAIR*image of the brain), and wherein the segmentation aims to delineate each WM lesion in the MRI brain image, each delineated WM lesions being then extracted from the different contrasts acquired for the lesion, e.g. from the first, second, and combination of the first and second image, in order to create the image patch for the different contrasts acquired for the lesion. For this purpose, a known in the art technique or segmentation algorithm might be used, as described in the paper of Roy S. et al. [7]. According to the present invention and in particular, each MR brain lesion image includes thus a selected set of voxels (e.g. representing a cube with an edge length of 21 voxels) representing a single WM lesion, preferentially surrounded by a predefined margin configured for delineating or identifying a (predefined, e.g. cubical) contour of the WM lesion. Each MR brain lesion image is thus preferentially an image patch extracted from a 3D MRI image of a brain by applying a segmentation mask onto the 3D MRI image, the latter resulting for instance from the combination of the first and second image, the segmentation mask enabling to select the set of voxels representing the WM lesion identified by the segmentation process. For instance, a segmentation algorithm configured for extracting each lesion in the form of a segmentation mask might be used for the extraction. Preferentially, for each lesion, the center of mass of the lesion is determined and the segmentation mask is automatically centered on the center of mass, enabling to extract for instance a cube of size $21 \times 21 \times 21$ voxels around the center of mass of the considered lesion for creating, for each acquired contrast, the image patch;

feeding a first subset of the set of the received or acquired 3D MR brain lesion images into a first machine learning (ML) algorithm, e.g. a first convolutional neural network (CNN), and a second subset of the set into a second ML algorithm, e.g. a second CNN, wherein the first and second ML algorithms are two different ML algorithms, e.g. wherein the first CNN and second CNN are two different CNNs. Preferentially, the first subset is identical to the second subset. Preferentially, the first subset and second subset are identical to the set. According to the present invention, and in particular, each of the first ML algorithm (e.g. CNN) and second ML algorithm (e.g. CNN) might thus receive as input a different subset of the set of 3D MR images. According to the present invention, the first ML algorithm, e.g. the first CNN, is configured for performing a classification of the 3D MR brain lesion images included in the first subset into a first class or a second class, wherein the first class includes or refers to CVS-positive (CVS+) lesions, as well as CVS-negative (CVS−) lesions (i.e. lesions identified as CVS+ lesions are classified in the first class and lesions identified as CVS− lesions are also classified in the first class), and the second class includes or refers to CVS excluded (CVSe) lesions, wherein the first CNN is configured for outputting, for each first subset received as input and each class (i.e. the first class and the second class), a probability that the brain lesion image first subset belongs to the class. A standard radiological definition of a central vein is commonly used and notably defined by Sati et al. in reference [4]: CVS+ lesions are lesions that exhibit a single central vein (only one and not more), CVS− lesions are lesions that exhibit no vein, CVSe lesions are lesions that should be excluded from the CVS assessment. CVSe lesions include confluent lesions (without vein) and/or lesions with multiple veins and/or lesions with eccentric veins and/or confluent lesions with vein(s). Such lesions are categorized in CVSe lesions.

According to the present invention, the second ML algorithm, e.g. the second CNN, is configured for performing a classification of the 3D MR brain lesion images included in the second subset into a third class or a fourth class, wherein the third class includes or refers to CVS+ lesions and the fourth class includes or refers to CVS− lesions, wherein the second ML algorithm, e.g. second CNN, is configured for outputting for each second subset received as input and each class (i.e. the third class and the fourth class), a probability that the subset belongs to the class, wherein the two ML algorithms (e.g. the first and second CNNS) are preferentially both CVSNet CNN [3] or based on the CVSNet architecture, and;

for each first subset and second subset that has been fed into respectively the first and second ML algorithm, e.g. CNNs, using the probability results obtained from the first and second ML algorithms, e.g. CNNs, as inputs to a final classifier configured for performing a final classification of the brain lesion image set into the second, third, or fourth class, wherein for each of the classes (i.e. second, third and fourth classes), the final classifier is configured for outputting a final probability that the image set belongs to the concerned class. Preferentially, the final classifier uses a random forest classifier or algorithm;

providing through an interface, e.g. a display, the class, among the second, third and fourth class, that is characterized by the highest probability value or result. Optionally, the method includes automatically calculating a fraction F of the CVS+ lesions, wherein F=number of CVS+ lesions divided by the sum of the number of CVS+ and number of CVS− lesions, and if the latter exceeds a predefined threshold, automatically suggesting to a user, or starting, an additional examination, e.g. by using the MRI system, or automatically launching an additional imaging of one or several lesions identified as CVS+ lesions, or automatically sending a signal to a warning device, the signal being configured for triggering a warning, e.g. visual and/or auditive warning, by the warning device.

In the proposed approach, the task of lesion exclusion (i.e. distinguishing CVS+/− from CVSe lesion types) and the task of vein detection (i.e. distinguishing CVS+ from CVS−) are separated in two individual tasks, i.e. are completely independent, each being performed by a dedicated individual classifier, i.e. the first and second ML algorithms which are preferentially and respectively the first CNN and the second CNN, specifically trained for that purpose. The output probabilities of these classifiers are then used as input to a second level classifier, i.e. the final classifier, e.g. random forest classifier, that performs the final classification into CVS+, CVS− and CVSe lesion classes. This task separation allows to train the different classifiers more specifically for their corresponding task resulting in better performance. The above-mentioned method is then preferentially repeated sequentially for all lesions identified/detected, e.g. during the segmentation process, in a 3D MR image of a whole brain.

With the objects of the invention in view, there is concomitantly provided a system or apparatus configured for carrying out the steps of the previously described method, the system comprises for instance an MRI system or a connection to an MRI system or to a database for acquiring the brain lesion images, a processing unit and a memory, wherein the processing unit is configured for automatically carrying out the above-mentioned method, and an interface, e.g. a display, for outputting, for each image that has been processed according to the method, the class associated to the highest probability, and/or for outputting a calculated fraction of CVS+ lesions.

The foregoing has broadly outlined the features and technical advantages of the present disclosure so that those skilled in the art may better understand the detailed description that follows.

Additional features and advantages of the disclosure will be described hereinafter that form the object of the claims. Those skilled in the art will appreciate that they may readily use the concept and the specific embodiment disclosed as a basis for modifying or configuring other structures for carrying out the same purposes of the present disclosure.

Although the invention is illustrated and described herein as embodied in a method and a system for automated central vein sign assessment, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
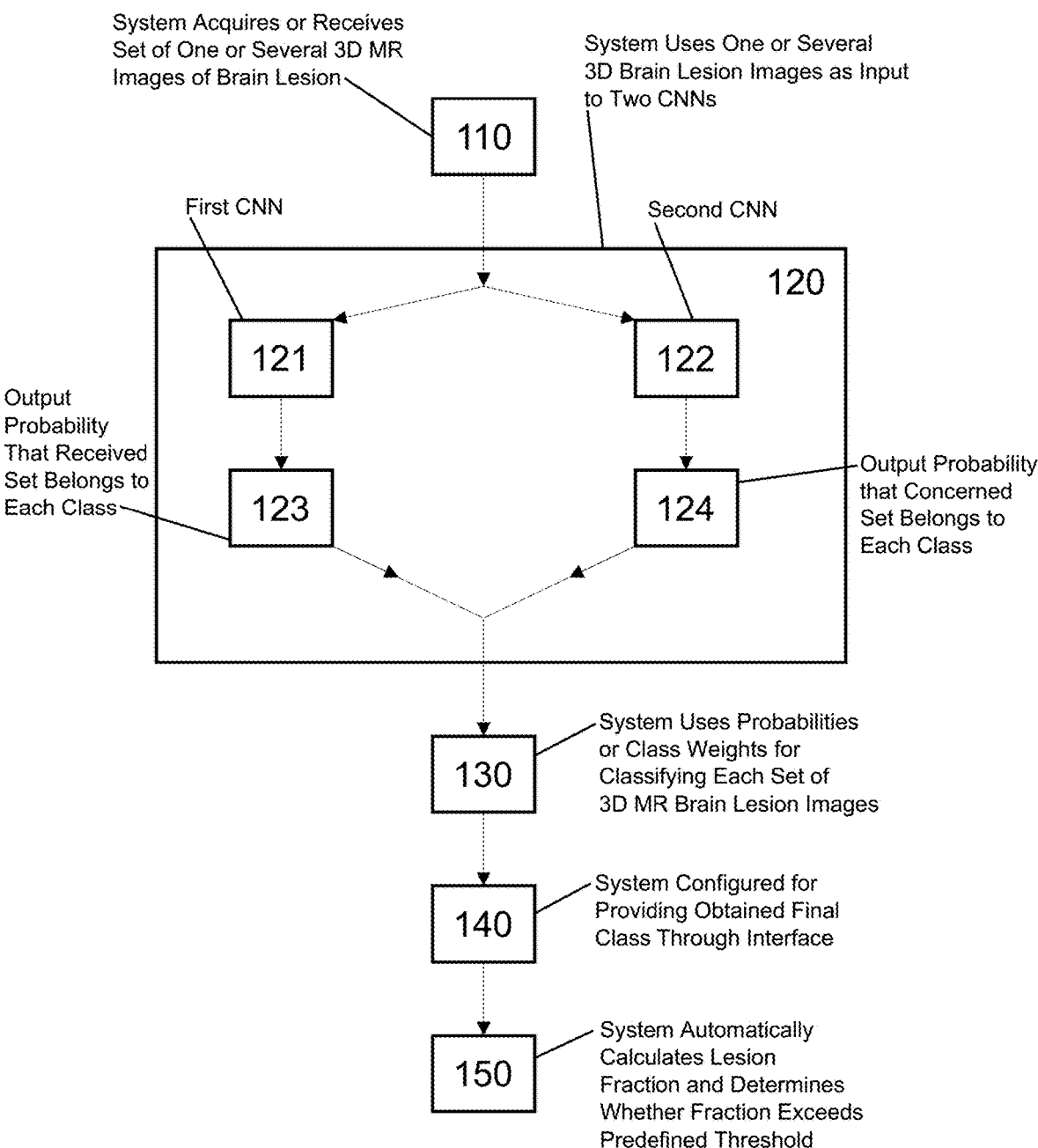
FIG. 1 is a flowchart of a method according to the invention.
Figure 2:
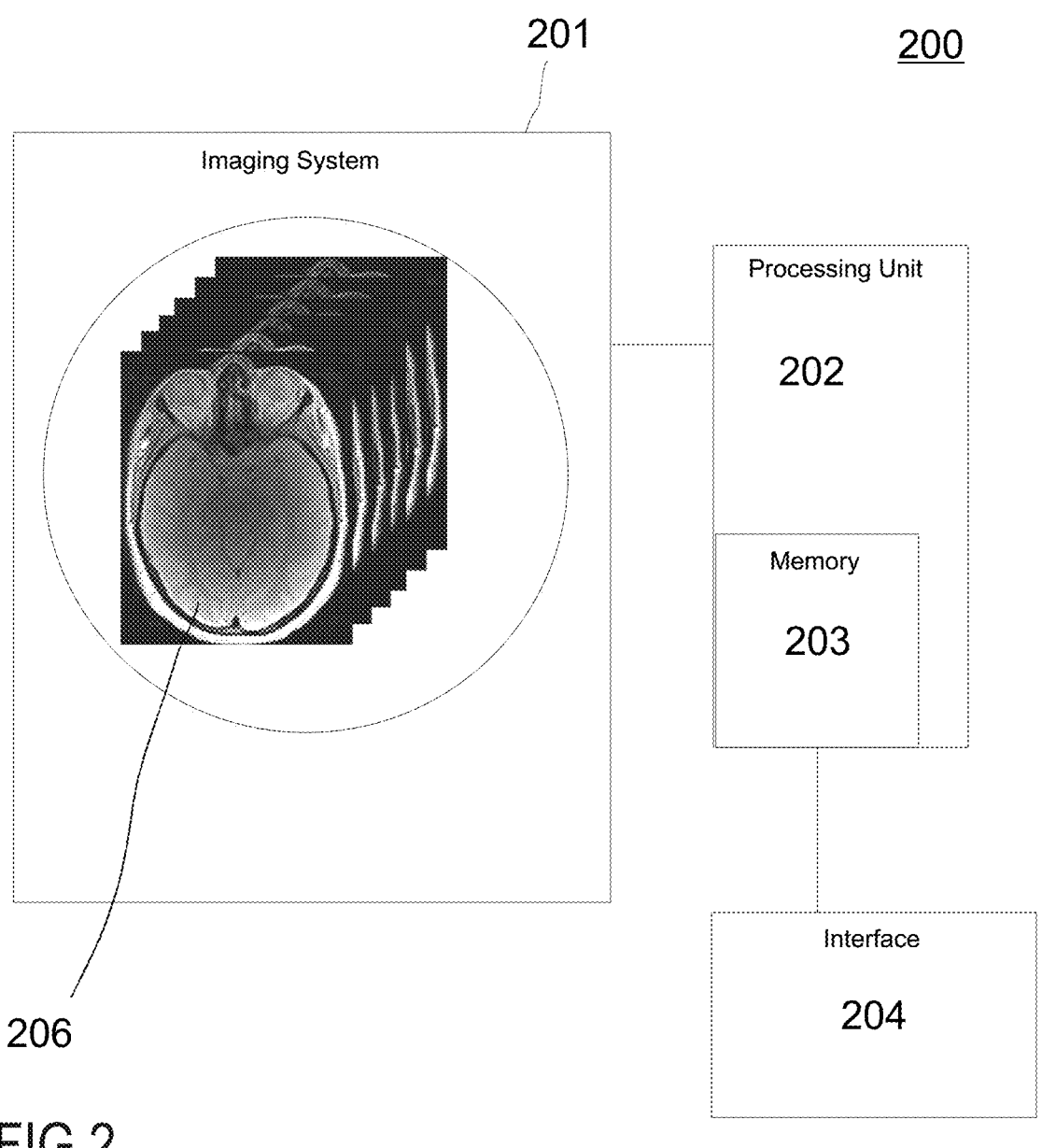
FIG. 2 is a schematic and block illustration of a system according to the invention.

Referring now to the figures of the drawings in detail and first, particularly, to FIG. 1 thereof, there is seen a schematic illustration of a workflow of a preferred embodiment of the method according to the invention. FIG. 2 schematically illustrates a system 200 for automated assessment of the CVS according to the invention. The system 200 includes:

optionally, an imaging system 201, e.g. a CT imaging system, e.g. an MRI apparatus, for acquiring images 206 of a brain lesion. The images might also be acquired from another imaging system, or from a database, or uploaded in the system according to the invention;

a memory 203 for storing the acquired images 206;

a processing unit 202 including a processor, the processing unit 202 being configured for processing the acquired images 206. The processing unit 202 is typically connected to the imaging system 201 and to the memory 203, and/or includes an acquisition interface for acquiring or downloading the images. The processing unit 202 preferentially includes the memory 203;

an interface 204, e.g. a display for displaying the acquired images 206 and/or reporting a calculated fraction of CVS+ lesions over all eligible (i.e. not CVSe) WM lesions.

The system 200 according to the invention is characterized in that its processing unit 202 is configured for carrying out the steps of the method according to the invention, wherein the interface is configured for providing, for each brain lesion image set, the class associated with the highest probability. The method will now be described in more detail with reference to FIG. 1.

At step 110, the system 200 according to the invention acquires or receives a set of one or several 3D MR images of a brain lesion. For instance, an MRI system 201 is configured for performing a 3D T1 weighted MPRAGE imaging before a contrast agent is injection, followed by a 3D T2*weighted segmented EPI imaging during an injection, and a 3D T2-weighted FLAIR imaging after injection, wherein a FLAIR*image is then generated by combining the T2-weighted FLAIR image and T2*-weighted segmented EPI image. The image processing for generating FLAIR*images is described for instance in reference [8] and is known in the art. Preferentially, the system according to the invention is then further configured for automatically segmenting brain lesions in the acquired or processed images, e.g. in the FLAIR*images. In other words, the images acquired by the MRI system might undergo different image processing for improving the detection, location, and classification of MS lesions performed in the following steps. In particular, the system 200 acquires the set of one or several images of a brain lesion by performing a segmentation process on at least one of the MR images acquired by the MRI system, from the segmentation, creating a mask for the concerned lesion, and using the mask for extracting the brain lesion image patch (i.e. the mask enabling selection in each image of the same set of voxels) from one or several of the images acquired by the MRI system 201, and/or one or several images resulting from a combination of the images acquired by the MRI system. Therefore, for a same lesion, the acquired 3D brain lesion images are preferentially image patches of the lesion, each patch representing a different MRI contrast, wherein at least one patch results from, or is based on, a T2*-based contrast imaging and another patch results from, or is based on, a WM lesion contrast MRI imaging, or wherein at least one patch results from, or is based on, a combination of an image obtained by using the T2'-based contrast imaging and another image obtained by using a WM lesion contrast MRI imaging.

At step 120, the system uses the one or several 3D brain lesion images acquired at step 110 as an input to two different CNNs, namely a first CNN 121 and a second CNN 122. Each of the CNNs may receive a different subset of the set of images as an input, e.g. the first CNN receives a first subset and the second CNN receives a second subset. Preferentially, the first and second CNN receive the same input. As shown in FIG. 1, the two CNNs are used "in parallel." For instance, they can receive the same input, but provide different outputs since the training they received has been different. Indeed, the first CNN 121 has been trained for detecting a presence of, or identifying, a lesion that has to be excluded from CVS assessment (i.e. for detecting or identifying a CVSe lesion), classifying each set of images received as input either in the class CVSe or in the class CVS+/−, and outputting 123, for each set of 3D brain lesion images received as input, the probability that the received set belongs to each class. The second CNN 122 has been trained for detecting a presence of, or identifying, a lesion that includes a single central vein (i.e. CVS+), classifying each set of images received as an input either in the class CVS+ or in the class CVS−, and outputting 124, for each received set, the probability that the concerned set belongs to each class.

Both the first and second CNNs are preferentially trained using a set of lesion samples (e.g. a set of image patches) as a training input, preferentially a first set for the first CNN and a second set for the second CNN, wherein the first and second sets are different, and, as a training output, for each lesion sample used as a training input, its classification into one of the two classes associated with the concerned CNN.

At step 130, the system uses the probabilities (or class weights) previously obtained for the classification of each set of 3D MR brain lesion images used as an input to respectively the first and second CNN, as an input to a final classifier. Indeed, from step 120, each received or acquired set can be associated to four probability values: from the first CNN 121 result, the probability P11 that the lesion represented in the images of the set belongs to the class CVS+/− and the probability P12=1-P11 that it belongs to the class CVSe; from the second CNN 122 result, the probably P21 that the lesion belongs to the class CVS+ and the probability P22=1-P21 that it belongs to the class CVS−. The probability values are used as an input in the final classifier. Advantageously, using the probabilities makes sure that all information of the first classification stage can be fully exploited for the final classification. For the latter, the final classifier has been trained for classifying each set in one of the three classes of lesions, CVS+, CVS−, and CVSe, using as an input the probabilities values, and outputting the class (called hereafter "final class") for which the brain lesion image set got the highest probability to belong to.

At step 140, the system 200 is configured for providing, through the interface 204, the obtained final class.

At step 150, and optionally, the system 200 automatically calculates a CVS+ lesion fraction and automatically determines whether the fraction exceeds a predefined threshold, e.g. 40% of the total number of eligible (i.e. non CVSe) lesions, and if exceeding the threshold is detected, then the system 200 preferentially automatically triggers a warning.

Preferentially, the final classifier might be replaced by a final CNN using, in addition to the probability/weights results of the first and second CNN, the set of brain lesion images as an input, wherein the brain lesion images are preferentially, as explained earlier, 3D patches extracted around the lesion from at least one of the following contrasts and received as separate input channels for the first, second, and optionally the final CNN: FLAIR*, and/or T2', and/or lesion mask, and/or CSF, and/or gray/white matter concentration maps, obtained for instance from a partial-volume estimation algorithm as described in Roche, et al. [9].

To summarize, the present invention proposes a multi-level classification architecture for automated CVS assessment, wherein the task of classifying lesion types is separated into two sub-tasks of identifying CVSe lesions and distinguishing CVS+ and CVS−, followed by a third classification step that uses the results of the first two classifiers as an input.

The following is a summary list of abbreviations and the corresponding structure used in the above description of the invention.

LIST OF ABBREVIATIONS

CVS central vein sign
MRI magnetic resonance imaging
MR magnetic resonance
MS multiple sclerosis
CSF cerebrospinal fluid
MPRAGE magnetization prepared rapid gradient-echo
FLAIR fluid-attenuated inversion recovery
CNN convolutional neural network
EPI echo planar imaging
ML machine learning

LIST OF CITATIONS

[1] Solomon A J, Bourdette D N, Cross A H, et al. The contemporary spectrum of multiple sclerosis misdiagnosis. Neurology 2016 (87): 1393-1399.
[2] Fartaria M J. Cvsnet: A deep learning-based approach for automated detection of the central vein sign. Mult. Scler. J. 2019.
[3] Maggi P, Fartaria M J, Jorge J, et al. CVSnet: A machine learning approach for automated central vein sign assessment in multiple sclerosis, NMR Biomed. 2020.
[4] Sati P, Oh J, Todd Constable R, et al. The central vein sign and its clinical evaluation for the diagnosis of multiple sclerosis: A consensus statement from the North American Imaging in Multiple Sclerosis Cooperative. Nat. Rev. Neurol. 2016.
[5] Dworkin J D, Sati P, Solomon A, et al., Automated integration of multimodal MRI for the probabilistic detection of the central vein sign in white matter lesions, Am. J. Neuroradiol. 2018.
[6] Huelnhagen et al., Toward Fully Automated Assessment of the Central Vein Sign Using Deep Learning, Proc. Intl. Soc. Mag. Reson. Med. 29 (2021), 0488.
[7] Roy S, Butman J A, Reich D S, Calabresi P A, Pham D L. Multiple sclerosis lesion segmentation from brain MRI through fully convolutional neural networks. arXiv: 1803.09172 2018.
[8] Sati P, George I C, Shea C D, Gaitan M I, Reich D S. FLAIR*: A combined MR contrast technique for visualizing white matter lesions and parenchymal veins. Radiology 2012, doi: 10.1148/radio1.12120208.
[9] Roche A, Forbes F. Partial Volume Estimation in Brain MRI Revisited BT-Medical Image Computing and Computer-Assisted Intervention—MICCAI 2014: 17th International Conference, Boston, MA, USA, Sep. 14-18, 2014, Proceedings, Part I. In: Gotland P, Hata N, Barillot C, Hornegger J, Howe R, editors. Cham: Springer International Publishing; 2014. pp. 771-778.

The invention claimed is:
1. A method for automatically detecting, in a magnetic resonance image, a white matter lesion exhibiting a central vein sign, the method comprising steps of:
acquiring a set including one or several 3D MR images of a brain lesion;
using a system for automated assessment of the central vein sign, the system including a processing unit and a memory, and the system:
using a first and a second subset of the set as a respective input to a first and a second machine learning algorithm, the first machine learning algorithm and the second machine learning algorithm being two different machine learning algorithms;
configuring the first machine learning algorithm for performing a classification of the first subset into a first class or a second class, the first class including central vein sign +lesions and central vein sign −lesions, and the second class including central vein sign e lesions, the first machine learning algorithm being further configured for outputting, for the first subset received as an input and each class, a probability that the subset belongs to the class;
configuring the second machine learning algorithm for performing a classification of the second subset into a third class or a fourth class, the third class including central vein sign +lesions and the fourth class including central vein sign −lesions, the second machine learning algorithm being further configured for outputting for the second subset received as an input and each class, a probability that the second subset belongs to the class;

for each set, using probability results obtained from the first and second machine learning algorithms as inputs to a final classifier configured for performing a final classification of the set into the second, third, or fourth class, and for each of the classes, configuring the final classifier for outputting a final probability that the set belongs to the class; and providing, through an interface, a class, among the second, third and fourth classes, being characterized by a highest probability value.

2. The method according to claim 1, which further comprises acquiring at least one image of the set by using a T2*-based contrast imaging technique.

3. The method according to claim 2, which further comprises providing the at least one image as a FLAIR* image.

4. The method according to claim 1, which further comprises:

acquiring one or several brain images by using an MRI system;

automatically performing a brain lesion segmentation in at least one of the acquired images for segmenting the brain lesion;

creating a segmentation mask for the brain lesion from the segmentation; and using the segmentation mask for acquiring from one or several of the images acquired by the MRI system, the set of one or several 3D MR images of the brain lesion.

5. The method according to claim 1, which further comprises providing the first and second machine learning algorithms as a central vein sign Net convolutional neural network or based on a central vein sign Net architecture.

6. The method according to claim 1, which further comprises using a random forest classifier or algorithm for the final classifier.

7. The method according to claim 1, which further comprises:

providing the 3D MR images used as an input to at least one of the first or the second machine learning algorithms as 3D patches extracted around the brain lesion;

the set including at least one or several 3D patches extracted from a modality selected from a group including: at least one of FLAIR*, or T2*, or lesion mask, or cerebrospinal fluid, or gray matter concentration map, or white matter concentration map.

8. The method according to claim 1, which further comprises automatically calculating a fraction of the central vein sign +images, and determining whether the fraction exceeds a predefined threshold.

9. The method according to claim 8, which further comprises automatically triggering at least one of a visual or auditive warning upon the fraction exceeding the predefined threshold.

* * * * *